(12) United States Patent
Balmer

(10) Patent No.: US 7,988,934 B2
(45) Date of Patent: Aug. 2, 2011

(54) CARRIER FOR POSITIONING OBJECTS IN RELATION TO LABORATORY ARTICLES

(75) Inventor: Johannes Balmer, Wetzikon (CH)

(73) Assignee: Tecan Trading AG, Mannedorf (CH)

( * ) Notice: Subject to any disclaimer, the term of this patent is extended or adjusted under 35 U.S.C. 154(b) by 1087 days.

(21) Appl. No.: 11/739,163

(22) Filed: Apr. 24, 2007

(65) Prior Publication Data

US 2007/0251341 A1 Nov. 1, 2007

Related U.S. Application Data

(60) Provisional application No. 60/745,868, filed on Apr. 28, 2006.

(51) Int. Cl.
*B01L 3/02* (2006.01)

(52) U.S. Cl. ........ 422/509; 422/63; 422/501; 73/864.25

(58) Field of Classification Search .................. 422/100, 422/63–67, 501, 509–511; 73/864.01–864.25
See application file for complete search history.

(56) References Cited

U.S. PATENT DOCUMENTS

| | | | |
|---|---|---|---|
| 3,518,533 A | | 6/1970 | Arnelo |
| 4,971,536 A | * | 11/1990 | Takeda et al. .............. 418/206.5 |
| 2004/0076550 A1 | * | 4/2004 | Ruedisser et al. ............ 422/100 |

FOREIGN PATENT DOCUMENTS

| | | |
|---|---|---|
| CH | 464566 | 10/1968 |
| EP | 147 815 | 11/2004 |
| EP | 1477815 | 11/2004 |
| GB | 25084 A | 0/1904 |
| GB | 356140 A | 9/1931 |
| GB | 504982 A | 5/1939 |
| WO | WO 02/059626 | 8/2002 |
| WO | WO2004/030504 A1 * | 4/2004 |
| WO | WO 2004/100177 | 11/2004 |

* cited by examiner

*Primary Examiner* — Jan M Ludlow
(74) *Attorney, Agent, or Firm* — Notaro, Michalos & Zaccaria P.C.

(57) ABSTRACT

Relates to a carrier (1) for positioning objects (5), which are oriented in the Z direction of a coordinate system, in relation to laboratory articles. Z rods (12) comprise a Z guide (43), on a cage (10) carrying the individual drive wheel (17), on which the Z rod (12) is guided in the Z direction. Each drive wheel (17) comprises a section (41), which is tailored to the cross-section of the profiled rod (18) of the Z drive of the carrier (1), individually driven by a motor, on which the drive wheel (17) is seated so it is not rotatable and is displaceable by sliding in the Y direction. The carrier (1) is characterized in that the attack faces (40) of the profiled rods (18) for driving a drive wheel are larger than the attack faces of a profiled rod having a square cross-section but having equally large radius.

15 Claims, 5 Drawing Sheets

Prior art
Fig. 3
Fig. 4A
Fig. 4B
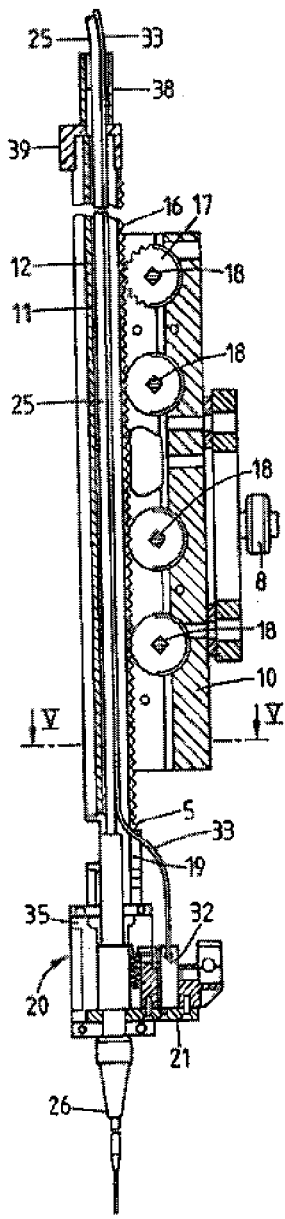
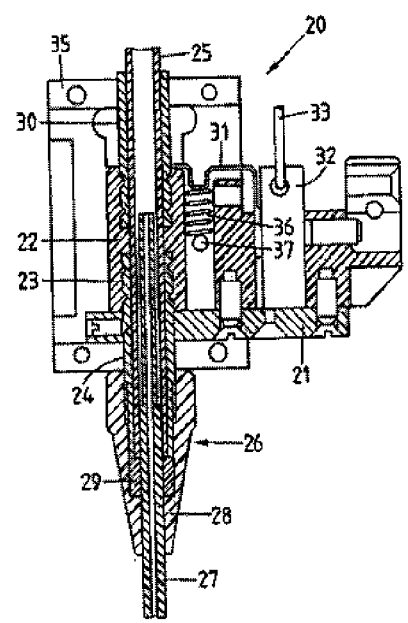
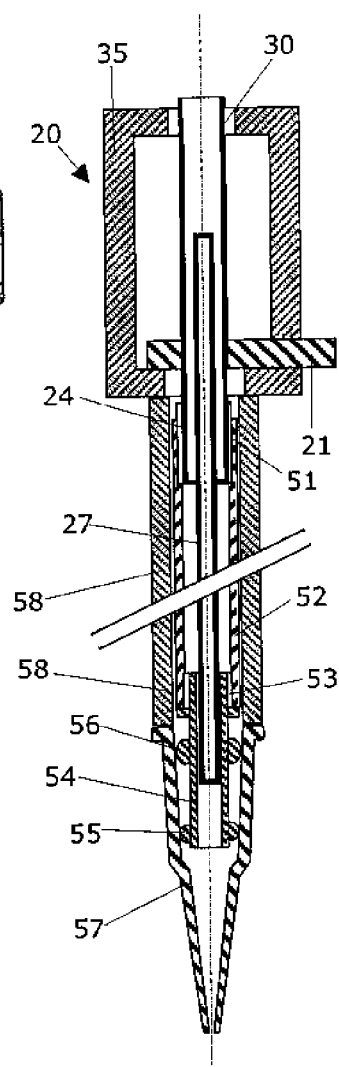
Fig. 5
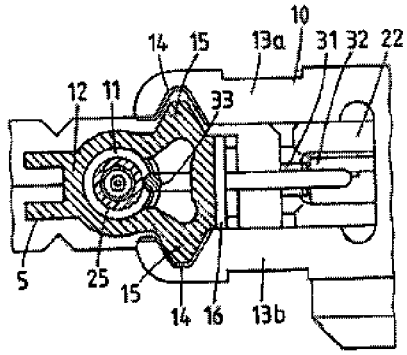

CARRIER FOR POSITIONING OBJECTS IN RELATION TO LABORATORY ARTICLES

RELATED APPLICATIONS

This patent application claims priority of the U.S. Provisional Application No. 60/745,868 filed on Apr. 28, 2006, the entire disclosure of which is incorporated herein in its entirety for all purposes.

RELATED FIELD OF TECHNOLOGY

The present invention relates to carriers for positioning objects which are oriented essentially vertically in the Z direction of a coordinate system in relation to laboratory articles. Each of these objects is individually received on a Z rod. Each of these Z rods is oriented essentially identically to these objects and is situated so it is movable along an axis running essentially horizontally in the Y direction of this coordinate system. Each of these Z rods is implemented so it is essentially vertically movable, in that it has teeth which are engaged with a drive wheel, driven by a motor, of a Z drive of the carrier, which comprises at least one profiled rod situated essentially horizontally and in the Y direction. In addition, each Z rod comprises a Z guide, which is situated on a cage supporting an individual drive wheel, the Z rod being guided by sliding on this Z guide in the Z direction. Each drive wheel comprises a section which is tailored to the cross-section of the profiled rod of the Z rod of the carrier individually driven by a motor, on which the drive wheel is seated so it is non-rotatable and is displaceable by sliding in the Y direction. In addition, each profiled rod comprises attack faces, which exert a contact pressure force on corresponding counter faces of the section of a drive wheel to drive this drive wheel.

RELATED PRIOR ART

Work platforms for handling liquids, for example, for pipetting liquids from containers and for distributing the liquids into the wells of a microplate have devices according to the species and are known, for example, from the documents WO 02/059626 A1 and EP 1 477 815 A1. These are preferably work platforms in which, for example, a pipette tip may be automatically positioned at a specific location. In particular, EP 1 477 815 A1 discloses especially precise positioning of objects in relation to the 1536 wells of a microplate, so that damage to a pipette tip, a temperature sensor, a pH probe, or another oblong, thin object which is to be positioned in a well, due to impact on the walls of the wells and/or the surface of the microplate may be prevented. In addition, sample losses and the contamination of neighboring samples or the workspace may thus be practically precluded. A precise approach to the well, in which no danger of unintended contact of parts of the microplate exists, is therefore a basic requirement for routine work using a liquid handling system, which may be used for automatically assaying blood samples, for example. A precise approach is not only to be ensured in the essentially horizontal plane of a Cartesian coordinate system defined by the X and Y directions; the Z or height position of a functional tip of an oblong, thin object, such as a pipette tip, a temperature sensor, a waveguide, or a pH probe is also to be able to be positioned as precisely and reproducibly as possible in a Cartesian or also a polar coordinate system.

OBJECTS AND SUMMARY OF THE PRESENT INVENTION

An object of the present invention is thus to provide an alternative device, using which objects oriented essentially vertically in the Z direction of a coordinate system may be positioned precisely and reproducibly to a high degree in relation to laboratory articles, in particular in the Z direction.

This object is achieved according to the features of independent claim 1. The invention is characterized in that in the carrier described at the beginning, the attack faces of the profiled rods for driving a drive wheel are larger than the attack faces of a profiled rod having a square cross-section but having equally large radius.

Particularly preferred embodiments are characterized in that in the carrier described at the beginning, the attack faces of the profiled rods have at least one of the following features:
(a) a concave element;
(b) an at least partially curved face;
(c) an at least partially planar face, which encloses an intermediate angle of at most 40° with the closest largest radius of the profiled rod.

Preferred embodiments and further features according to the present invention result from the additional dependent claims.

In connection with the present invention, "concave" is understood to mean that there is a depression in the cross-section of the profiled rod in relation to a plane that links the two largest radii lying closest to one another.

BRIEF INTRODUCTION OF THE DRAWINGS

The device according to the present invention will be explained in greater detail on the basis of schematic figures of exemplary embodiments which do not restrict the scope of the present invention.

FIG. 3 shows an enlarged detail from a section along section line III-III in FIG. 1;

FIG. 4A shows an enlarged detail from FIG. 3 having inserted pipetting needle;

FIG. 4B shows an enlarged detail corresponding to FIG. 4A, but having inserted disposable pipette tip;

FIG. 5 shows an enlarged detail from a section along section line V-V in FIG. 3;

Figure 8A:
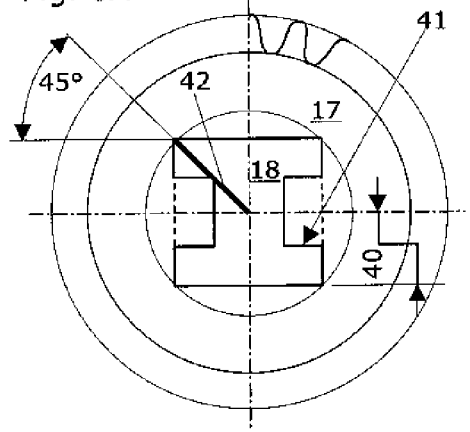
Figure 8B:
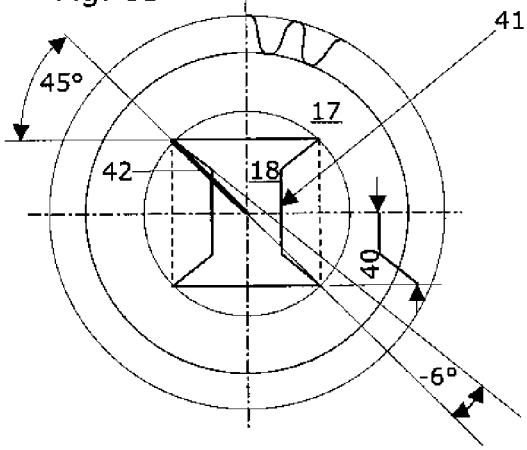
Figure 9:
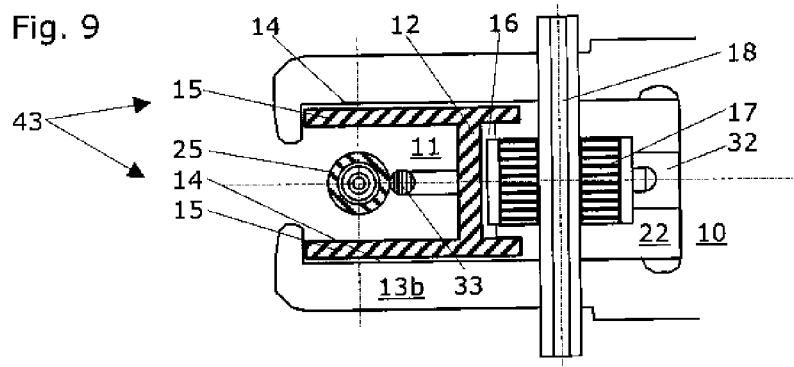
Figure 10A:
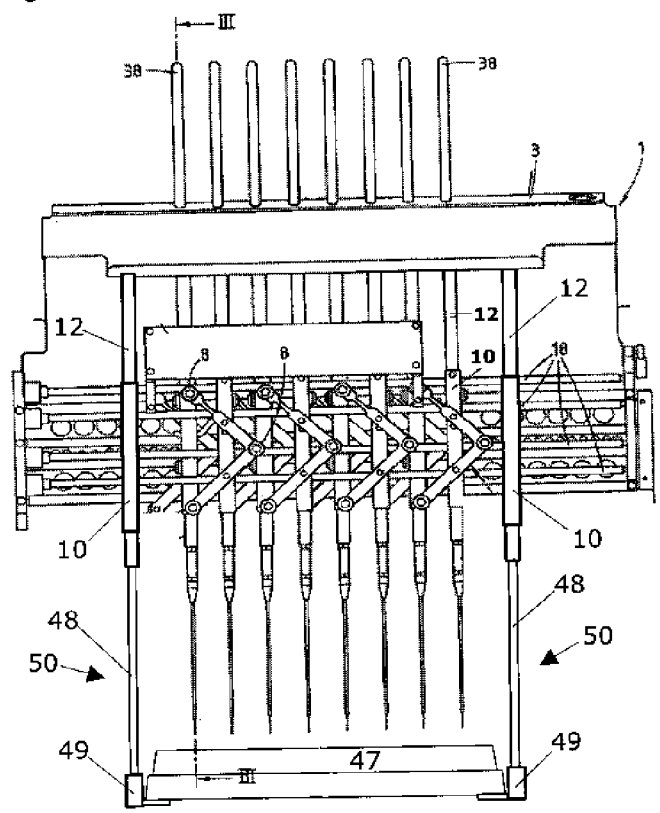
Figure 10B:
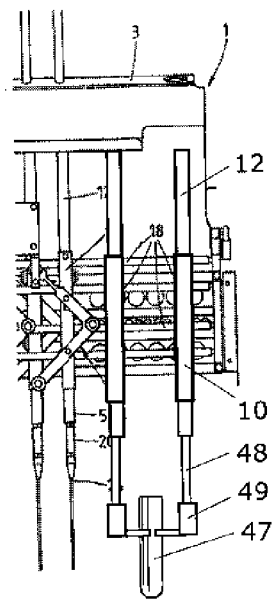
Figure 11A:
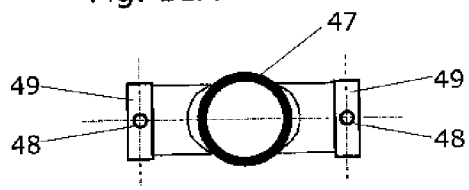

FIG. 7 shows symmetrical, star-shaped cross-sections of profiled rods according to the present invention:
  FIG. 7A showing a three-pointed star,
  FIG. 7B showing a four-pointed star,
  FIG. 7C showing a five-pointed star,
  FIG. 7D showing a six-pointed star having partially planar attack faces running parallel to the largest radius, and
  FIG. 7E showing a six-pointed star without planar attack face parts;

FIG. 8 shows further cross-sections of profiled rods according to the present invention:
  FIG. 8A showing a recumbent H, and
  FIG. 8B showing an upright I;

FIG. 9 shows a horizontal section through an alternative, H-shaped Z rod having a Z guide;

FIG. 10 shows side views of a carrier having a pipetting device known from the prior art (WO 02/059626 A1), various parts, above all the housing, being at least partially removed:

FIG. 10A showing a combination with a gripper according to the present invention for microplates, and FIG. 10B showing a combination with a gripper according to the present invention for sample tubes or tools;

FIG. 11 shows horizontal sections through a special object implemented as a gripper arm half:

FIG. 11A showing a first embodiment, for gripping sample tubes or tools, and

Figure 11B:
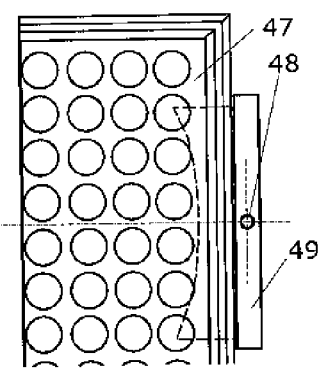

FIG. 11B showing a second embodiment, for gripping microplates or identification instruments.

DETAILED DESCRIPTION OF THE INVENTION

Figure 1:
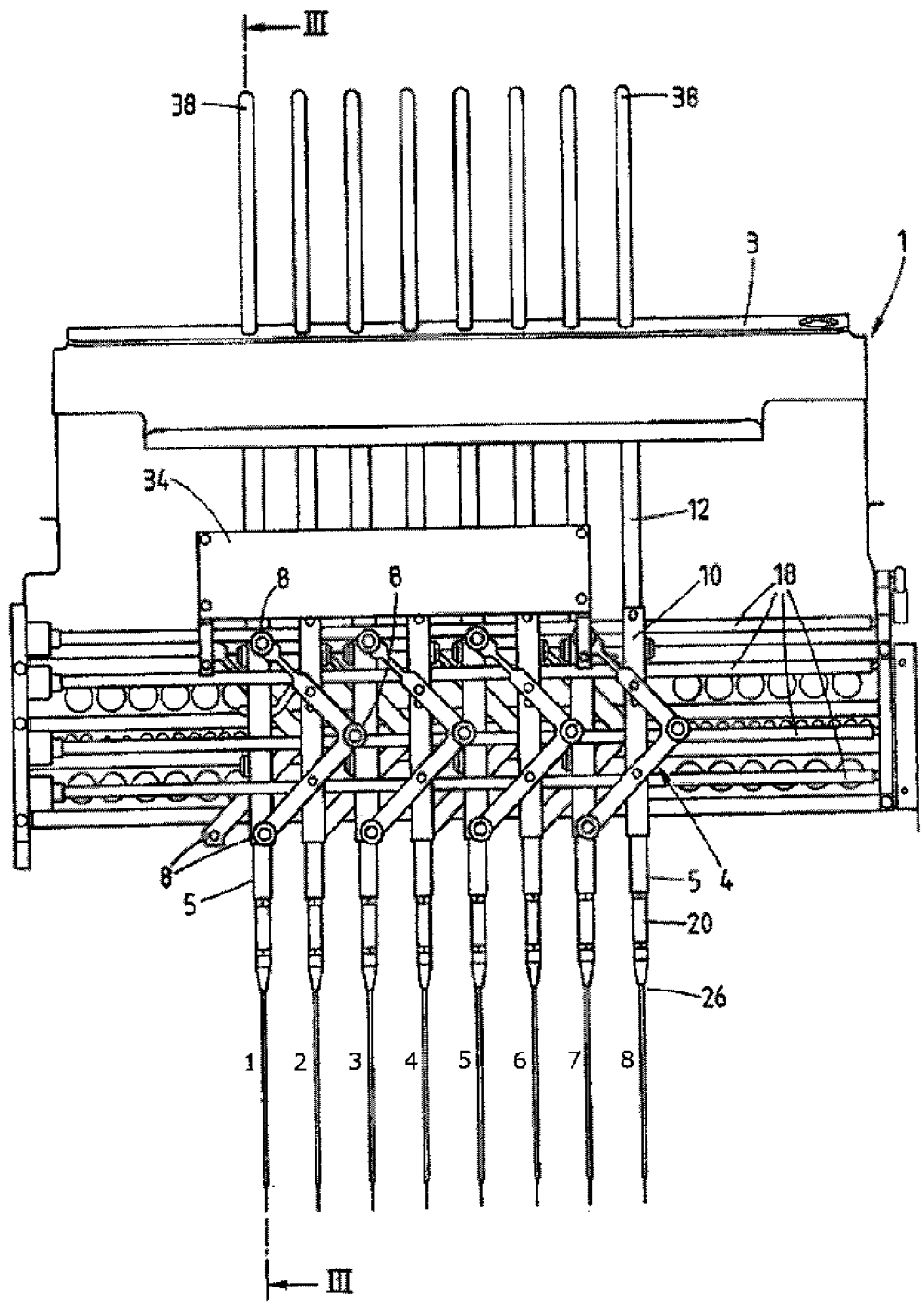
FIG. 1 shows a side view of a carrier of a known pipetting device from the prior art (WO 02/059626 A1), various parts, above all the housing, being at least partially removed.
Figure 2:
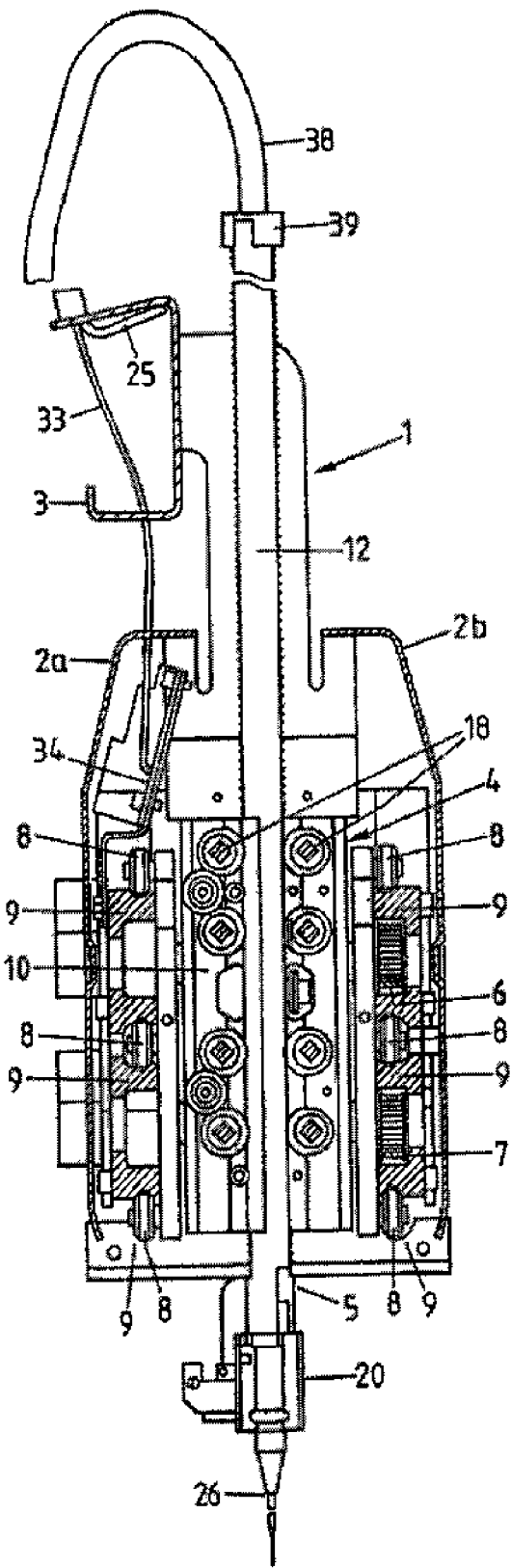
FIG. 2 shows a section through this carrier from the prior art.

FIG. 1 shows a pipetting device known from the prior art (WO 02/059626 A1), which comprises an oblong carrier 1 (cf. also FIG. 2). This carrier 1 comprises a C-profile 3 connected thereto and a housing, which comprises two shells 2a,b and is situated below the C-profile 3. The carrier 1 is suspended so it is transversely displaceable, so that it may be displaced in a controlled way over a work surface of a work platform for handling liquids. Laboratory articles 47 known per se, such as microplates, troughs, sample tubes, and racks for receiving sample tubes, may be situated and/or positioned on such a work surface (not shown). A carriage 4, which carries eight pipettes 5 situated in a row, is mounted in the carrier 1 so it is longitudinally displaceable. More or less pipettes 5 may also be situated in such a row. In connection with the present invention, pipettes are referred to as objects 5 oriented essentially vertically in the Z direction of a coordinate system. Objects of this type are not restricted to pipettes. Typical objects are, for example, reference tips or pipetting needles for mutual adjustment and/or orientation of microplates and other vessels in relation to a coordinate system of a liquid handling system which comprises a work surface. Dispenser tips and pipette tips are also such objects, spray needles also being referred to as dispenser tips, for example. Fixed steel cannulas, disposable tips made of plastic, and so-called "ZipTips®" (Millipore Corporation, 80 Ashby Road, Bedford, Mass. 01730-2271, U.S.A.) are referred to here as exemplary pipette tips. Electrodes, temperature sensors, pH probes, and optical fibers and other waveguides, such as endoscopes, are also included in the preferred objects to be positioned.

The carriage 4 may be longitudinally displaced by parallel movement of two toothed belts 6,7 in the carrier 1, rolls 8, which are situated on both sides in three rows lying one on top of another, rolling on rails 9 attached to the housing. The carriage 4 may also be stretched and compressed on location by opposing movement of the toothed belts 6,7 (cf. FIG. 2), so that the spacing and/or axial spacing between neighboring pipettes or planar objects 5 change in the same way. In particular, directly driving those pipettes or objects which are seated at position 1 or 8 (numbered from left to right in FIG. 1) has proven itself. All pipettes or objects are connected to one another here using a "Luxembourg grating", so that their spacing to one another—independently of stretching or compression—is always essentially equally large. Instead of eight pipettes, two, four, six, or twelve pipettes 5 are preferably also situated on a carrier 1.

Each of the pipettes or objects 5 (see FIGS. 1, 2, 3, and 5) is mounted so it is vertically displaceable on a holder implemented as a vertical profile, a so-called cage 10. Each of the pipettes 5 comprises a pipette housing, which is implemented as a vertical Z rod 12 enclosing a channel 11. This Z rod is guided according to a first, preferred embodiment in the holder and/or in the cage 10 between two guide arms 13a,b having grooves 14 facing toward one another, in which webs 15 of the Z rod 12 engage.

Each Z rod 12 has continuous teeth 16 from the upper end up to the proximity of the lower end, in which a drive wheel 17 implemented as a gearwheel engages. The drive wheel 17 is plugged onto a profiled rod 18 which preferably, but not exclusively extends overall over the length of the carrier 1, so it is non-rotatable but longitudinally displaceable, so that it is also displaced by the cage 10. These profiled rods 18 are preferably each individually driven by a motor (not shown). The Z rod 12 may therefore be raised and lowered by rotating the corresponding profiled rod 18—and thus the drive wheel 17, which engages with its teeth 16.

A single drive wheel 17 is preferably seated on a profiled rod 18, so that each individual Z rod 12 may be moved individually in the vertical direction. If two or more Z rods 12 are to be moved simultaneously and identically in the vertical direction, this may be performed by simultaneously driving the corresponding individual profiled rod 18 and drive wheel 17 (cf. FIGS. 1 through 3). Notwithstanding this embodiment, two or more drive wheels 17 may also be situated jointly on a single profiled rod 18, so that multiple Z rods 12 may be moved coupled to one another in the Z direction (not shown). In spite of jointly situating multiple drive wheels 17 on a profiled rod 18, the spacing of the Z rods 12, which are driven via these drive wheels 17, to one another may be varied; these drive wheels 17 are therefore also situated so they are displaceable in the Y direction on the profiled rod 18 but are non-rotatable in relation to this profiled rod 18.

According to a second, alternative embodiment (see FIG. 9), this Z rod 12 is implemented as a H profile. In this case, the teeth 16 are situated as internal teeth on this H-profile. The Z guide 43 comprises two webs 15 projecting forward in the X direction and extending in the Z direction of the Z rod 12, which are mounted to slide in grooves 14 of arms 13a,b of an assigned cage 10 carrying the individual drive wheel 17.

Notwithstanding the illustration in FIGS. 1 and 2, two special objects 50 which are also oriented essentially vertically in the Z direction of a coordinate system are positionable in relation to laboratory articles 47 may also be attached to the carrier 1 (cf. FIGS. 10 and 11). Each of these special objects 50 is individually received on one Z rod 12 and is movable in the Y and Z directions like the objects 5. However, the cages 10 and the special objects 50 are preferably not connected via an "Luxembourg grating" to the cages 10 of the remaining objects 5, but rather are displaceable practically independently thereof not only in the Z direction but rather also in the Y direction (cf. FIG. 10). These special objects 50 each comprise a gripper rod 48 having at least one gripper finger 49 for grasping laboratory articles 47, such as sample tubes (cf. FIG. 11A) microplates (cf. FIG. 11B), racks for sample tubes, troughs (both not shown), and the like. These laboratory articles are grasped jointly by the two special objects 50, which may be identified as "half of a gripper arm" because they are equipped with gripper rod 48 and gripper finger 49, and may be lifted and put down at an arbitrary location on the work surface of the work platform or onto devices located thereon, such as "carriers" for microplates or "racks" for sample tubes. The two "halves of a gripper arm" having gripper rod 48 and gripper finger 49 must be situated on one side of the pipette assembly and implemented correspondingly for grasping and transporting sample tubes, or also tools and/or identification instruments, such as barcode readers and the like (cf. FIG. 10B).

Together with the special objects 50, such a carrier preferably comprises a total of 10 objects 5, 50, i.e., two gripper arm halves and 8 pipettes (cf. FIG. 10). All objects 5 do not have to be equipped identically to one another, arbitrary combinations of pipettes, electrodes, temperature sensors, pH probes, waveguides, and the like may thus be selected. For example, a configuration on a single carrier 1 may be selected which comprises four pipettes, a pH probe, a temperature sensor, a waveguide, and an electrode, two of the special objects 50 implemented as gripper halves also alternately being able to be situated.

The teeth 15 terminate just above the lower end of each Z rod 12. These teeth 15 have an opening 19 adjoining there, through which the channel 11 is accessible. A head 20 is attached at the lower end of the Z rod 12, which comprises a baseplate 21 made of metal (see, for example, FIG. 4). A molded part 22 made of an electrically insulating material, preferably plastic, is attached to this baseplate 21 (cf. FIG. 4A). A vertical continuous channel 23 penetrates both the baseplate 21 and also the molded part 22. A lower collar 24 made of metal is situated in the lower section of this channel 23, which encloses connection tubing 25 made of plastic. The collar 24 and the connection tubing 25 are guided through the baseplate 21 and project beyond its bottom side.

A pipette tip 26 is plugged onto the lower collar 24 (cf. FIG. 4A). The pipette tip 26 comprises a tube 27, tapering toward the bottom, which projects inside the connection tubing 25 into the channel 23. The pipette tip 26 additionally comprises a conical union nut 28, which presses externally against the lower collar 24. This union nut 28 receives the lower part of the lower collar 24. In addition, the pipette tip 26 comprises a ring 29 situated at the lower end of a recess of the union nut 28, which comprises electrically conductive material. The tube 27 comprises electrically conductive plastic or metal and is electrically connected to the baseplate 21 via the ring 29 and the lower collar 24. The connection tubing 25 is enclosed above the lower collar 24 by an upper collar 30 made of metal, whose lower part lies in the channel 23. This upper collar 30 projects into the Z rod 12 and/or between the two H legs 15 of the Z rod 12. This upper collar 30 is spaced apart and electrically insulated from the lower collar 24. The upper collar 30 is electrically connected via a tab 31 to an external contact of a plug 32, which is plugged into a recess of the molded part 22 extending up to the baseplate 21.

A shielded cable 33 originates from the plug 32, which leads to a circuit 34 (see FIGS. 1,2), and whose grounded shielding is electrically connected via the external contact of the plug 32 and the tab 31 to the upper collar 30. The core of the cable 33 is connected to the baseplate 21 and via this to the tube 27 of the pipette tip 26. The head 20 also comprises a slider 35 which is vertically displaceable in a limited way in relation to the baseplate 21 and the molded part 22, and which is impinged using a force acting downward by a coiled spring 36 supported on the tab 31, which presses against a transverse bolt 37. However, it is held fixed in the position shown by the plug-on pipette tip 26.

If the pipette tip 26 is lowered into a vessel filled with liquid, such as a cavity of a microtitration plate or another laboratory article 47, as soon as the tip of the tube 27 contacts the liquid level, the capacitance between this liquid level and the part electrically connected thereto on one hand and the grounded parts on the other hand changes suddenly. These parts electrically connected to the liquid level are connected via the core and the grounded parts are connected via the shielding of the cable 33 to the circuit 34 (see FIG. 1).

This capacitance change is registered by the circuit 34 to detect the liquid level and may be used to control the pipetting device. For example, the lowering of the corresponding pipette tip may be stopped and aspiration of the liquid may be initiated. If no pipette tip is plugged on, the slider 35 is in a lower position (not shown), in which the transverse bolt 37 rests on the baseplate 21, so that a short circuit is produced by the coiled spring 36, which is also registered by the circuit 34. Notwithstanding the use of transverse bolt 37 and coiled spring 36 just described, this short circuit may also be produced in the liquid level detection circuit, which indicates the lower position of the slide 35, by a reed switch (not shown).

As an alternative to the pipetting needle shown in FIG. 4A, an adapter tube 52 may also be screwed onto the same device, in particular onto the lower collar 24 over its external thread 51 (cf. FIG. 4B). This adapter tube 52 also carries an internal thread 53 on its bottom side, onto which a receptacle cone 54 for a disposable pipette tip 57 may be screwed on up to its stop. This receptacle cone 54 simultaneously holds the tube 27 in position. The receptacle cone 54, which otherwise has a constant cross-section, has two annular thickened places 55, 56 on its exterior, on which the pipette tip 57 is pressed snugly, so that it is seated securely sealed, because the thickened places 55, 56 slightly deform the pipette tip 57. The control sleeve 58 is raised by plugging on the pipette tip 57. This raising of the control sleeve brings the slider 35 into its upper position, so that the circuit of the liquid level detection is open. When a pipette tip 57 is ejected, the control sleeve 58 falls onto its lower stop on the receptacle cone 54 and the slider 35 falls into its lower position, the circuit of the liquid level detection is thus short-circuited.

Elastic envelope tubing 38 adjoins the upper end of the Z rod 12 (cf. FIG. 3). This envelope tubing 38 is connected using a connection sleeve 39 to the Z rod 12 in such a way that a vertical starting direction is applied to it. A further, lower part of this connection sleeve 39 is plugged onto the Z rod 12 and the envelope tubing 38 is pulled over the narrow upper part of this connection sleeve 39. The envelope tubing 38 is guided to the carrier 1, more precisely to the top side of the C profile 3, where its opposite end is attached. The attachment may also be implemented in such a way that the adjoining section of the envelope tubing 38 has an approximately vertical starting direction applied thereto. The self-supporting implementation of this envelope tubing in combination with the two at least essentially vertically applied starting directions ensures displacement of the pipettes or other objects 5 in the Y direction, without this elastic envelope tubing 38 being able to tangle.

The connection tubing 25 runs through the channel 11 in the Z rod 12 and further into the interior of the envelope tubing 38 and through an opening in the C profile 3 into the interior thereof, where it is guided onto the end of the carrier 1. The cable 33 originating from the plug 32 is also drawn into the channel 11 through the opening 19 in the lower end of the Z rod 12, runs through the channel to the upper end of the Z rod 12 and further into the interior of the envelope tubing 38 also into the interior of the C profile 31 from which it is drawn further through further openings therein and in the shell 2a to the circuit 34.

As described above, the profiled rod 18 exerts a contact pressure force using its attack faces 40 on corresponding counter faces of the section 41 of a drive wheel 17 to drive this drive wheel 17. It has been shown that a special implementation of these attack faces 40 of the profiled rod 18 may be significant for the precision and reproducibility with which objects oriented essentially vertically in the Z direction of a coordinate system may approach a specific Z position. In particular, it has been shown that this precision and reproducibility is influenced by the shape of the cross-section of such profiled rod 18. Thus, the hysteresis of a Z drive typically resulting after several million strokes may be reduced to approximately 60% by changing the square cross-section known from the prior art (cf., for example, WO 02/059626 A1) to a six-pointed, star-shaped cross-section (cf. FIG. 7E).

Such a star-shaped cross-section (cf. FIG. 7), which is preferably made of profiled rod 18 manufactured from steel, is preferably achieved using eroding, casting, extruding, cold shaping, milling, or grinding and combines all features required in Claim 1:

(a) the attack faces 40 of the profiled rod 18 having a star-shaped cross-section comprise a concave element 44, in that a depression is provided in relation to a face which connects the two largest radii lying closest to one another;

(b) the attack faces 40 of the profiled rod 18 having a star-shaped cross-section comprises an at least partially curved face 45, in that the "points of the star" are rounded; and (c) the attack faces 40 of the profiled rod 18 having a star-shaped cross-section comprises an at least partially planar face 46, at least one planar part of these attack faces 40 enclosing an intermediate angle of at most 40° with the closest largest radius 42 of the profiled rod 18.

Figure 7A:
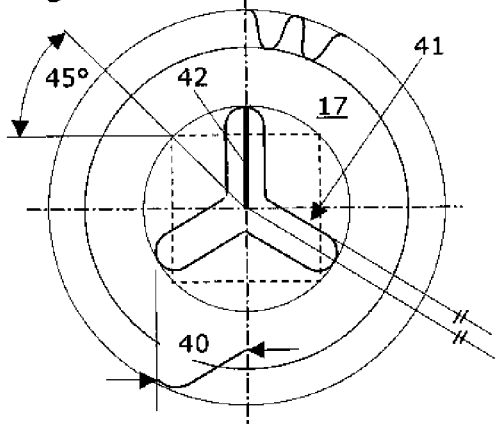

In the embodied of the profiled rod 18 according to the present invention shown in FIG. 7, this intermediate angle is actually significantly less than 40°, namely as low as 0° (cf. FIG. 7A in particular). The course of this attack face 40 in an essentially star-shaped cross-section of the profiled rod 18 may deviate arbitrarily from a face parallel to the largest radius, as long as one of the conditions for the cross-sectional shape just formulated is fulfilled; the entire effective surface of the profiled rod 18 may be free of planar faces (cf. FIG. 7E in particular). In the latter illustration, the cross-section of each star beam is reduced along the largest radius 42 with increasing distance from the center of symmetry and rotation of the profiled rod 18. Notwithstanding this illustration, it is especially preferable for the cross-section of the star beams to have a maximum which is not located at their beginning (as shown) but rather between their beginning and their end (not shown).

Figure 6A:
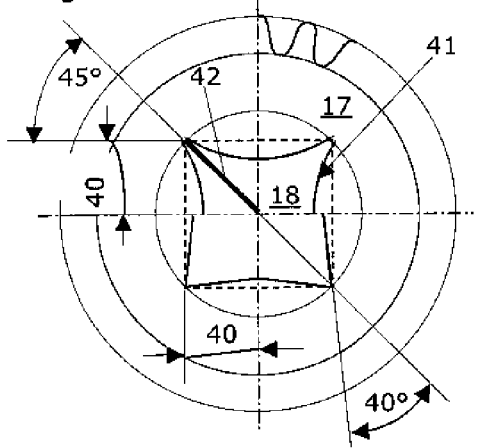
FIG. 6A showing a diamond-shaped cross-section having curved and/or planar faces, and
  FIG. 6B showing a triangular cross-section having planar and/or concave faces.
Figure 6B:
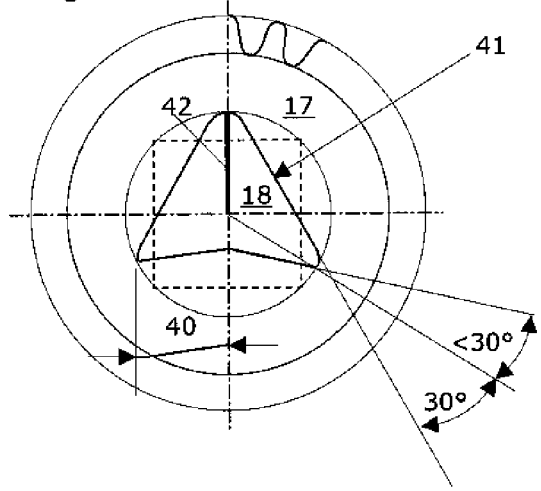
FIG. 6 shows polygonal cross-sections of profiled rods according to the present invention.
Figure 7B:
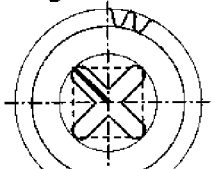
Figure 7C:
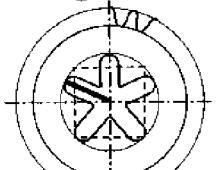
Figure 7D:
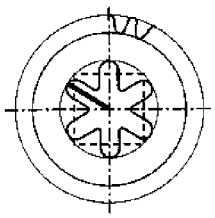
Figure 7E:
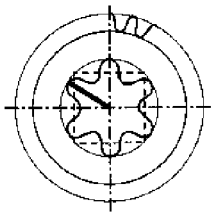

FIG. 7A shows a three-pointed star, FIG. 7B shows a four-pointed star, FIG. 7C shows a five-pointed star, and FIG. 7D and FIG. 7E show a six-pointed star. The largest radius 42 in the cross-section of the profiled rod 18 is marked bold in all FIGS. 6 through 8. The angle between the at least one planar part of these attack faces 40 and the closest largest radius 42 of the profiled rod 18 is specified in all FIGS. 6 through 8, the square cross-section known from the prior art being indicated by dashed lines in each case.

FIG. 6 shows various polygonal cross-sections of profiled rod 18 according to the present invention. FIG. 6A shows a diamond-shaped cross-section having curved (upper half of image) and planar (lower half of image) faces. In FIG. 6A, for direct comparison, the corners of the diamond-shaped cross-sections precisely correspond to the corners of the square cross-section known from the prior art. In FIG. 6B, triangular cross-sections having planar (upper half of image) and concave (lower half of image) faces are shown. FIG. 8A shows a cross-section of the profiled rod 18 in the form of a recumbent "H" and FIG. 8B shows such a cross-section in the form of an upright "I".

All cross-sections shown have symmetry; of course, asymmetrical cross-sections having, for example, a F, H, L, or K shape also belong in the scope of the present invention, which is based on the finding that the attack faces 40 of the profiled rod 18 according to the present invention for driving a drive wheel 17 are to be larger than a profiled rod having a square cross-section but having equally large radius 42. If this requirement is fulfilled, the local surface pressure and thus the strain and deformation of the drive wheel 17 are reduced. Concave elements are especially preferred, because these allow the mass of the drive wheel 17 and the attack faces 40 to be enlarged. Equipping carriers 1 with profiled rods 18 according to the present invention is especially important if the pipette tips of the work platform are to be used for so-called piercing of rubber closures attached to laboratory articles 47. This piercing is performed using forces in the kg range, which strains the drive wheels 17 severely.

All of the attack faces 40 marked in FIGS. 6 through 8 relate to attack faces 40 which act counterclockwise upon rotation of the drive wheel 17. Even if all elements are not described in all figures, identical reference signs identify identical or corresponding elements.

List of Reference Signs:

1 carrier
2*a,b* shell
3 C profile
4 carriage
5 object, pipette, etc.
6,7 toothed belt
8 roll
9 rail
10 cage
11 channel
12 Z rod
13*a,b* arm
14 groove
15 web
16 teeth
17 drive wheel
18 profiled rod
19 opening
20 head
21 baseplate
22 molded part
23 channel
24 lower collar
25 connection tubing
26 pipette tip
27 tube
28 union nut
29 ring
30 upper collar
31 tab
32 plug
33 cable
34 circuit
35 slider
36 coiled spring
37 bolt
38 envelope tubing
39 connection sleeve
40 attack face
41 section
42 largest radius
43 Z guide
44 concave element
45 curved face
46 planar face
47 laboratory article
48 gripper rod
49 gripper finger
50 special object 51 external thread
52 adapter tube
53 internal thread
54 receptacle cone
55 annular thickening
56 annular thickening
57 disposable pipette tip
58 control sleeve

What is claimed is:

1. A carrier for positioning objects oriented essentially vertically in the Z direction of a coordinate system in relation to laboratory articles, each of the objects being individually received on a Z rod, and each of the Z rods:
being oriented essentially identically to these objects and being situated so that the Z rod is movable along an axis running essentially horizontally in the Y direction of this coordinate system;
being implemented as movable essentially vertically, in that the Z rod has teeth which are engaged with a drive wheel, driven by a motor, of a Z drive of the carrier comprising at least one profiled rod situated essentially horizontally and in the Y direction;
comprising a Z guide, which is situated on a cage carrying an individual drive wheel, the Z rod being guided to slide on this Z guide in the Z direction; and
wherein each drive wheel comprises a section, which is tailored to the cross-section of the profiled rod, individually driven by a motor, of the Z drive of the carrier, on which the drive wheel is seated so that the drive wheel is not rotatable and is displaceable by sliding in the Y direction; and each profiled rod comprising attack faces which exert a contact pressure force on corresponding counter faces of the section of a drive wheel to drive this drive wheel, and
wherein the attack faces of the profiled rods for driving a drive wheel are larger than the attack faces of a profiled rod having a square cross-section but having equally large radius.

2. The carrier according to claim 1, wherein the attack faces of the profiled rods have at least one of the following features:
(a) a concave element;
(b) an at least partially curved face;
(c) an at least partially planar face, which encloses an intermediate angle of at most 40° with the closest largest radius of the profiled rod.

3. The carrier according to claim 1, wherein the Z rods are implemented as hollow profiles and the teeth are situated as external teeth on this hollow profile, the Z guide comprising two lateral webs projecting on the Z rod in the Y direction and extending in the Z direction, which are mounted to slide in grooves of arms of an assigned cage carrying the individual drive wheel.

4. The carrier according to claim 1, wherein the Z rods are implemented as an H profile and the teeth are situated as internal teeth on this H profile, the Z guide comprising two webs which project forward from the Z rod in the X direction and extend in the Z direction, which are mounted to slide in grooves of arms of an assigned cage carrying the individual drive wheel.

5. The carrier according to claim 1, wherein each of the individually driven drive wheels exerts a contact pressure force on the particular teeth of the Z rod.

6. The carrier according to claim 1, wherein several of these Z rods are situated at an axial distance neighboring one another along the axis running essentially horizontally in a Y direction, the axial spacing of these Z rods in the Y direction being able to be varied using Y drives of the carrier.

7. The carrier according to claim 6, wherein the axial spacing of these Z rods is essentially adaptable to the distance of the openings of laboratory articles, the objects being selected from a group which comprises reference tips, dispenser tips, pipette tips, electrodes, temperature sensors, pH probes, optical fibers, and waveguides.

8. The carrier according to claim 6, wherein the axial spacing of two of these Z rods is essentially adaptable to the external dimensions of a laboratory article, these two Z rods comprising a gripper rod and at least one gripper finger directed toward the other gripper rod for receiving at least one laboratory article, tool, or identification instrument.

9. The carrier according to claim 1, wherein the laboratory articles are selected from a group which comprises microplates, troughs, racks for receiving sample tubes, and sample tubes.

10. The carrier according to claim 1, wherein the carrier is implemented as movable in the X direction of this coordinate system.

11. The carrier according to claim 1, wherein the profiled rods of the carrier comprise at least two identically shaped attack faces for each rotational direction.

12. The carrier according to claim 1, wherein the profiled rods of the carrier have an essentially star-shaped cross-section.

13. The carrier according to claim 1, wherein the carrier comprises at least one head having a slider which is vertically displaceable in a limited way in relation to a base plate and a molded part, this slider being held in an upper position by a screwed-on union nut for fixing an object or by a control sleeve, which is pushed up by a plugged-on disposable pipette tip, so that a circuit for liquid level detection is kept open.

14. The carrier according to claim 13, wherein the slider, if not held in the upper position by a screwed-on union nut or by a pushed-up control sleeve, is in a lower position, so that a short-circuit is produced in the circuit for liquid level detection, which is registered by a circuit.

15. A liquid handling system having at least one work surface and comprising at least one carrier according to claim 1.

* * * * *